United States Patent [19]

Lagin

[11] Patent Number: 4,683,601
[45] Date of Patent: Aug. 4, 1987

[54] MEDICAL PILLOW

[76] Inventor: Herbert Lagin, 31 Deer Park Rd., Great Neck, N.Y. 11021

[21] Appl. No.: 910,409

[22] Filed: Sep. 22, 1986

[51] Int. Cl.$^4$ .............................................. A47G 9/00
[52] U.S. Cl. ......................................... 5/431; 5/443; 128/132 R
[58] Field of Search ................... 5/437, 436, 434, 443, 5/435, 431, 432; 297/195; 138/132 R, 128

[56] References Cited

U.S. PATENT DOCUMENTS

| | | | |
|---|---|---|---|
| 1,580,210 | 4/1926 | McCulloch | 5/436 |
| 3,327,330 | 6/1967 | McCullouch | 5/437 |
| 4,197,604 | 4/1980 | Nakamura | 5/437 |
| 4,235,472 | 11/1980 | Sparks et al. | 5/434 |
| 4,393,520 | 7/1983 | Koch | 5/436 |
| 4,512,047 | 4/1985 | Johnson | 5/432 |

Primary Examiner—Alexander Grosz
Attorney, Agent, or Firm—Schweitzer & Cornman

[57] ABSTRACT

A medical pillow for use by patients who have recently undergone an open heart surgical type operation which facilitates and eases the pain associated with coughing for the expectoration of phlegm from their lungs. The medical pillow comprises a central chest supporting and contacting area having a pair of laterally extending arm engaging wings connected thereto. A sleeve is provided on the outer surface of the chest contacting area. The patient's hands, after the patient's arms are first folded across the patient, are slid into the open ends of the sleeve and this enables the patient to grip and hold the medical pillow and easily pull the same against their chest to facilitate the coughing procedure. The medical pillow is also provided with arm cutout areas so that the individual's arms can easily be folded across their chest without discomfort and simultaneously the upper portions of the patient's arms when placed over the wings of the pillow bring the wings flush against the patient's sides. In an alternate use of the medical pillow, the pillow can be inverted with the otherwise neck supporting surface being placed between the patient's legs, the wings folding around the patient's waist or hips with the cut-out areas providing a spot for the patient's legs. In this manner, the medical pillow can be used for general comfort by patients who have recently undergone abdominal surgery.

7 Claims, 4 Drawing Figures

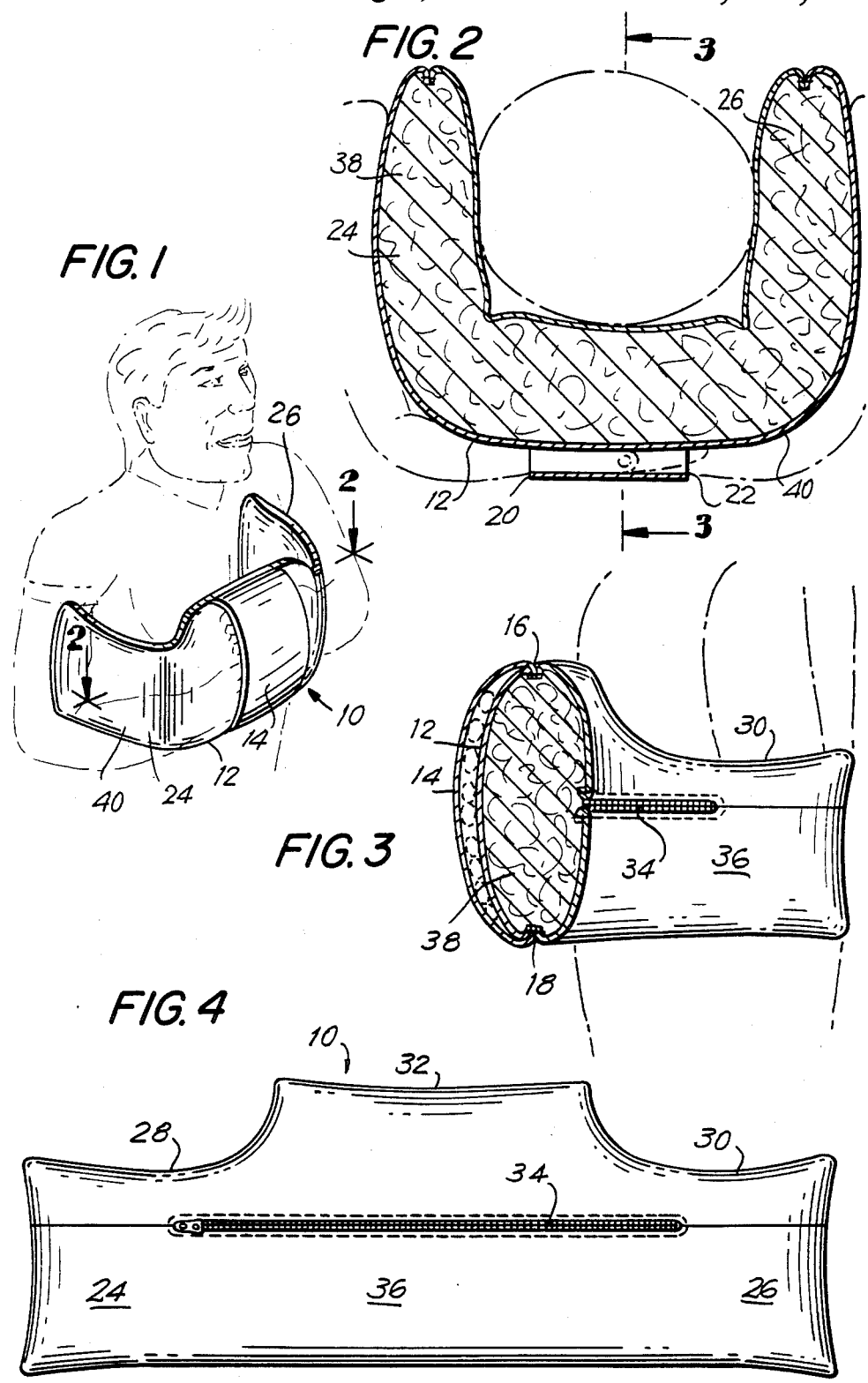

MEDICAL PILLOW

BACKGROUND OF THE INVENTION

The present invention relates to a medical pillow which is extremely useful in post operative care of patients who have undergone open heart and/or abdominal type surgery. The medical pillow allows the patient to place a flat and firm object against the patient's chest and gently grip, hold and/or pull the pillow against the chest while allowing the patient to cough, as desired or as required, and thereby bring up phlegm for expectoration. This is a voluntary "exercise" which for proper recuperation by the patient is performed to clear the lungs. The medical pillow is provided with a central chest contacting portion which is intended to be placed flush on the chest of the patient. The pillow is also provided with side or laterally extending wing portions which extend around the side of the patient and are held thereagainst by the upper portions of the patient's arms. The forearms of the patient are then folded across his or her front and the hands are placed within an open ended sleeve so that the patient can easily grip, hold and/or pull the chest pillow against his or her chest and thereby facilitate the voluntary coughing and subsequent patient expectoration of phlegm to clear the lungs or simply the pillow serves to relieve the pain associated with post operative care.

In addition, the pillow can be flipped over, i.e., turned upside down so that the otherwise neck contacting surface of the chest contacting portion (when the pillow is used subsequent to open heart surgery) is placed between the wearer's legs and the otherwise chest contacting surface (when the pillow is used after open heart surgery) is placed against the abdominal area of the patient. In this use of the medical pillow, the cut-out portions of the laterally extending side wings now conform over the patient's legs. Thus the pillow is placed against the abdominal area of the patient with the wings held against the patient's sides or hips to again relieve or alleviate the pain associated with post-operative surgery, in this case, abdominal surgery. Again, the patient's hands can be slid within the open ends of the sleeve to facilitate the placement, holding and gripping of the cardiac pillow against the selected area of the patient.

In addition, the medical pillow has yet another post operative use. Subsequent to the operation and after minimum of recuperation in the hospital, the patient can more comfortably and, certainly less expensively, fully recover at home. To facilitate transportation of the patient, either from hospital to home, home to wherever, etc. The patient can place the pillow against his or her chest or abdominal area (depending on the surgical operation performed) to provide additional cushioning within an automobile or other vehicle. The sleeve of the medical pillow is adapted to have the free end of the seatbelt pass therethrough and the seat belt can then be connected or buckled to the fixed point or hold down position of the vehicle. In this manner, the pillow is held over the patient's chest and an additional cushioning layer is provided to the patient which, again, provides relief to the patient; allows him to travel without fear and yet the pillow is held in relative position by the seatbelt passing through the open ended sleeve. The medical pillow has many other uses which should be readily apparent.

DESCRIPTION OF THE PRIOR ART

Post operative heart surgery necessarily requires that the patient, to alleviate and clear his or her lungs, intentionally cough up phlegm for subsequent expectoration. This procedure is now done by holding a conventionally available head pillow against the patient's chest. Generally this is accomplished by either the patient, himself, holding the head pillow against his chest or, alternatively, a family member or nurse will facilitate holding of the pillow. The use of a conventional head pillow, in the form of a simple soft rectangle shape, however, suffers from several disadvantages. More specifically, it is difficult for the patient to grip, hold and maintain the chest pillow in position while simultaneously pulling the chest pillow against his or her chest. The pulling-in action is important to alleviate pain, during coughing. In addition, the head pillows are generally only sufficiently wide to accommodate the head of the patient for resting or sleeping such that when a head pillow is held on the patient's chest no support is really provided to the sides of the patient. In addition, since the head supporting pillows are rectangle in shape, it is difficult and uncomfortable for the patient, even assuming the pillow is wide enough to wrap around the patient's sides, for him or her to hold the pillow around his upper torso since there is no empty area to accommodate the patients arms. Even a slight degree of discomfort for a patient who has recently undergone open heart surgery is a serious problem and should be avoided.

In addition, the conventionally used rectangularly-shaped head pillows are often soft since they are primarily intended to be used for supporting the patient's head and, therefore, they are really too soft for being held against the patient's chest to facilitate coughing and relieving pain. The medical pillow, described herein, is in the preferred embodiment of a sufficiently firmer interior stuffing material, more akin to an upholstery cushion, such that it greatly alleviates the pain of the patient and more easily allows for the expectoration of phlegm.

Also, the normally used head pillow, due to its' simple aforementioned rectangular shape, and its' relatively short over all height (again, necessitated by it being primarily used for support of the head during sleeping), will not, when placed against the chest, extend up to the patient's neck. This, again detracts from the patient's comfort. The present invention, on the other hand, as will be more fully explained hereinafter, provides, if desired, a neck supporting, smooth curved, upper surface of the chest contacting portion so that the patient can place the pillow against his chest and have his or her head rest on the smooth wall while performing the coughing procedure.

SUMMARY OF THE INVENTION

The present invention relates to a medical pillow and specifically the pillow has utility for patients who have recently undergone open heart or abdominal surgery. The medical pillow allows the patient to easily hold a firm cushion flushly and flatly against his or her chest, unaided, and thereby alleviate much of the pain incident to post operative surgery. In addition, as is usual in post-operative open heart surgery, the patient is expected to periodically and often clear his or her lungs by coughing up phlegm and expectorating the same. The medical pillow of the present invention allows this to be done by the patient himself without the aid of a family member or nurse, and without the use of the now conventionally used rectangularly-shaped, relatively soft head pillow. The present invention contemplates, in the preferred embodiment, that the inside stuffing material of the pillow be more in the nature of an upholstery pillow and not as soft as the inside stuffing of a head pillow.

The present medical pillow contemplates that a chest contacting surface be held flush against the patient's chest. The center chest contacting section is provided with laterally extending, arm engaging wing-like sections. These side sections or pillow wings wrap around the patient's chest to the sides of the patient and extend beneath the patient's arms. Arm cut-out areas are provided to the wings which allow the wearer's arms to easily and comfortably droop down and hold the pillow in a body conforming manner around the patient's chest and sides, without discomfort. The patient then folds his arms across his chest and slips his hands into the two-sided open end sleeve which is provided on the chest contacting surface and extending from top to bottom. The top of the medical pillow is, in an alternate embodiment, provided with a neck engaging smooth, curved wall surface which allows the patient to hang his head and have it supported on the pillow. This, again, eliminates much of the pain and discomfort otherwise incident to post-operative procedures of patients who have undergone open heart surgery.

In an alternate use of the medical pillow, the pillow can be inverted such that the otherwise neck engaging surface can be placed between the wearer's legs with the otherwise arm cutout sections passing over the patient's legs. The side wings can now be held against the patient's waist or hips. In this manner, patients who have undergone abdominal surgery can also be relieved of pain and be provided with support, while sitting up.

In yet another use of the medical pillow, a patient who has recently undergone either open heart or abdominal surgery can utilize the medical pillow when transporting himself in a vehicle without the discomfort and fear normally associated with seatbelts crossing over and directly overlying the area of operation. More specifically, the patient can sit in the seat of the automobile with the seatbelt first, before buckling, passing through the open ended sleeve such that the medical pillow is held against and in place on the patient's chest. Thus, the seatbelt does not press directly against the area of operation, the chest, but, rather, a firm cushioning material, in the form of a pillow, is interposed between the seatbelt and the wearer's chest or abdominal area. In this manner, the patient is relieved of much of the pain and fear otherwise associated with use of a seatbelt subsequent to surgery.

BRIEF DESCRIPTION OF THE DRAWINGS

FIG. 1 is a perspective view of the present invention as it is intended to be used, i.e., wrapped around the upper body of an individual, shown in phantom;

FIG. 2 is a cross sectional view of the present invention taken along lines 2—2 of FIG. 1;

FIG. 3 is a cross sectional view of the invention taken along lines 3—3 of FIG. 2; and FIG. 4 is a second embodiment of the present invention, not drawn to scale, and shows the curved wall which is useful for extending up to the patient's neck, as described below.

DETAILED DESCRIPTION OF THE INVENTION

A medical pillow, generally referred to by reference numeral 10 basically comprises a centrally located body contacting section 12 having a sleeve 14, in the preferred form, comprising an elastic piece of fabric material sewn to the top 16 and the bottom 18 of the body contacting section 12. As best seen in FIGS. 1 through 3, the body contacting section 12 is, in operation of use of the present invention, placed against a portion of the individual and, in its preferred use against the chest of the individual. The patient's arms are folded across his or her chest with the individual's hands slid into the open ends 20 and 22 of the sleeve 14. In this manner, the individual can hold the body contacting section 12 against his or her chest and thereby facilitate the providing of pressure against the chest, which, as mentioned, will faciliate the coughing up or expectoration of phlegm from the individual's lungs and the relief of pain due to that procedure. In the preferred embodiment of the present invention, the sleeve 14 is made of elastic material or fabric which facilitates the gripping and holding of the patient's hands and the pulling of the body contacting section 12 against the individual's chest. Also, in the preferred embodiment of the present invention, the dimensions of the body contacting section are approximately equal to an average individual's chest area.

Attached to and extending laterally from the centrally located, body contacting section 12 are laterally extending arm engaging wing-like members 24 and 26. In the preferred embodiment of the present invention, these arm engaging wing-like members 24 and 26 are, when the device is not being used, substantially uninterrupted extensions of the body contacting section 12. Also, as best seen in FIGS. 1 and 2, the arm engaging wing-like members 24 and 26, when the device is used, wrap around and conform to the individual's sides and are held firmly thereagainst by the individual's arm, resting over the arm engaging wing members. This, too, facilitates the compression of the chest cavity by the patient and the feeling of comfort provided by the pillow to patients. The arm engaging wing members 24 and 26 are provided with arm cut-out areas 28 and 30, respectively, which allow the individual's arms to be placed over the wing members in a comfortable manner. That is to say, when the invention is being used by an individual, with the wing-like members under the patient's arms, the cut-out areas lie directly beneath the individual's armpits and shoulders.

In the embodiment shown in FIGS. 1-3 of the drawings, the top surface 32 of medical pillow 10 is a smooth curved wall and lies across the individual's chest, but it should be appreciated that in the embodiment of the present invention shown in FIG. 4, top surface 32 can extend up to the individual's neck and provide a neck support which will again facilitate the expectoration of phlegm pursuant to post operative coughing techniques normally used and performed by cardiac patients.

According to the drawings of FIGS. 3 and 4, a zipper 34 is located in the rear 36 of the medical pillow 10 to facilitate removal of the stuffing material 38 from the medical pillow and to allow the outside surface 40 of the medical pillow to be selectively cleaned or washed between patients. It should be appreciated that the stuffing material 38, as well as the fabric for the outside surface 40 are sufficiently pliable such that the pillow will substantially conform to the outlined configuration of the patient when it is located around the individual's body portion and then pulled against it by the individual's hands.

In an alternate embodiment of the present invention, the arm engaging wing members 24 and 26, while connected to central section 12, are physically separated from the body contacting section 12 by fold-like seams 44 and 46 (not shown).

In use, by a patient who has recently undergone open heart surgery, the patient will place body contacting section 12 against his chest area with the arm engaging wing-like members 24 and 26 extending around and back along his sides, with his arms passing over the outside surface 40 of the arm engaging wing-like members to thereby cause the body contacting section 12 and the arm engaging wing-like members to substantially conform to the individual's sides and chest surfaces. Then, the individual's arms are crossed over one another (see FIGS. 1 and 2) with his hands slid into the open ends 20 and 22 of sleeve 14. Then, as directed by the physician or attendant, the patient can easily cough, expectorate phlegm or merely comfort himself while simultaneously decreasing the pain and fear associated with those procedures which normally are requried by patients who have open heart surgery or similar operations. The elastic sleeve member helps the patient hold the pillow in place and helps him pull the pillow against his chest for the "coughing" procedure.

In addition, and as a further advantage of the present invention, the medical pillow 10 can be easily inverted such that the top surface 32 extends between the patient's legs with the normally bottom surface 42 extending across the individual's stomach area. Here, again, the individuals hands will pass through the open ends 20 and 22 of the sleeve 14. In this manner, the same medical pillow which can be used for cardiac patients can also be used for patients who have undergone abdominal surgery. Here, again, a definite degree of comfort and decreased anxiety is provided to the patient. When so used, the arm cut-out areas extend over the patient's legs. Thus, a degree of versatility is provided by the above described medical pillow.

After the device has been used, where appropriate, the stuffing material 38 can be removed from the inside and the outside surface 40 can be washed, sanitized or otherwise cleaned. This is easily accomplished by opening up zipper 34 and removing the stuffing material and replacing the same after washing.

In yet another embodiment of the present invention, the central chest contacting section is filled with more stuffing material than the side extending wing-like members. In this manner, the chest of the patient is given sufficient support while simultaneously allowing the pillow to more easily conform around the sides of the patient.

In an alternate embodiment of the present invention, the medical pillow is provided with grommets at preselected locations. The grommets pass through the covering of the pillow. The grommets facilitate the outward passage of air from the interior of the pillow when the pillow is squeezed around the patient's torso and, in this manner, facilitate conformance of the pillow around the body.

In yet an alternate use of the medical pillow described herein, the patient can sit in an arm chair. The arm cut outs of the pillow can be located over the arms of the chair (the medical pillow is inverted) and pulled backwardly by the patient against his stomach area. This "forces" the patient to sit upwardly with his back flush against the straight back of the chair and in effect, pressure is taken off of the patient's front surgical area.

It should be understood, of course, that the specific form of the invention herein illustrated and described is intended to be representative only, as certain changes may be made therein without departing from the clear teachings of the disclosure. Accordingly reference should be made to the following appended claims in determining the full scope of the invention.

I claim:

1. A medical pillow for facilitating recovery from a surgical operation comprising:
   (a) a chest contacting section of sufficient size to accommodate a substantial portion of the patient's chest area;
   (b) a holding means connected to said chest contacting section to facilitate holding by the patient said chest contacting section against the chest area of the patient; and
   (c) a pair of underarm and patient side engaging wing sections, laterally extending from and connected to said chest contacting section which together with said chest contacting section, when said medical pillow is held by the patient, substantially conform to the patient's sides and chest area.

2. A medical pillow as claimed in claim 1, wherein said holding means is a two side open-ended sleeve overlying and located on the outside of said chest contacting section, capable of selective receipt of the hands of said patient.

3. A medical pillow as claimed in claim 2, wherein said sleeve is made of elastic fabric.

4. A medical pillow as claimed in claim 1, further comprising under arm cut-out portions for each of said wing sections.

5. A medical pillow as claimed in claim 4, wherein said pillow can be inverted for use such that said chest contacting section lies against the abdominal area of an individual, with said arm cut-out portions extending over the legs of said patient.

6. A medical pillow as claimed in claim 1, wherein said chest contacting section includes a smooth-walled neck-engaging surface.

7. A medical pillow as claimed in claim 1, wherein said chest contacting section is stuffed with more stuffing material than said wing sections.

* * * * *